United States Patent [19]

Crenshaw et al.

[11] 4,138,561

[45] Feb. 6, 1979

[54] CYANOCARBOXAMIDINES AND QUINAZOLINE PROCESS

[75] Inventors: Ronnie R. Crenshaw, Dewitt; George M. Luke, Lafayette; Richard A. Partyka, Liverpool, all of N.Y.

[73] Assignee: Bristol-Myers Company, New York, N.Y.

[21] Appl. No.: 838,417

[22] Filed: Sep. 30, 1977

[51] Int. Cl.$^2$ .......................................... C07D 239/95
[52] U.S. Cl. ............................ 544/284; 260/239 BC; 260/243.3; 260/302 H; 260/307 A; 260/332.3 R; 260/347.7; 544/291; 544/367; 544/369
[58] Field of Search ............ 260/243.3, 256.4 Q, 260/268 C, 268 CN, 239 BC, 302 H, 307 A, 332.3 R, 347.8, 347.7; 544/284, 291, 367, 369

[56] References Cited

U.S. PATENT DOCUMENTS 3,935,213  12/1973  Hess ................................ 260/256.4 Q

OTHER PUBLICATIONS

Curd et al., *J. Chem. Soc.*, 1759–1766 (1948).
Budesinsky et al., *Coll. Czech. Chem. Commun.*, 37, 2779–2785 (1972).
Ried et al., *Chem. Ber.*, 109, 2706–2715 (1976).

*Primary Examiner*—Paul M. Coughlan, Jr.
*Attorney, Agent, or Firm*—Robert H. Uloth

[57] ABSTRACT

Novel cyanocarboxamidines are disclosed. The new cyanocarboxamidines are particularly valuable as intermediates in the preparation of antihypertensive 4-amino-2-(4-substituted-piperazin-1-yl)-quinazolines.

20 Claims, No Drawings

CYANOCARBOXAMIDINES AND QUINAZOLINE PROCESS

FIELD OF THE INVENTION

This invention relates to new and useful N-cyano-N'-phenylcarboxamidines and to their chemical method of preparation. More particularly, the instant invention is concerned with use of the novel carboxamidine compounds as starting material for a one-step synthesis of antihypertensive agents such as the various 4-amino-2-(4-substituted piperazin-1-yl)quiniazolines described in U.S. Pat. Nos. 3,511,836; 3,669,968; 4,001,237; 4,001,238; copending U.S. Patent application Ser. No. 770,996, filed Feb. 22, 1977, now U.S. Pat. No. 4,101,548; and the 2-(4-substituted homopiperazino)-4-amino-6,7-dimethoxyquinazolines of U.S. Pat. Nos. 3,920,636.

DESCRIPTION OF THE PRIOR ART

F. H. S. Curd, et al., J. Chem. Soc., 1759 (1948) describes a procedure for the preparation of 2,4-dichloroquinazolines. As illustrated below, the Curd, et al. process involves cyclization of an ortho-ureido derivative (1) of various aromatic acids, amides, nitriles and esters with aqueous base or acid to form a 2,4-(1H,3H)quinazolinedione (2) which is chlorinated to the 2,4-dichloroquinazoline (3).

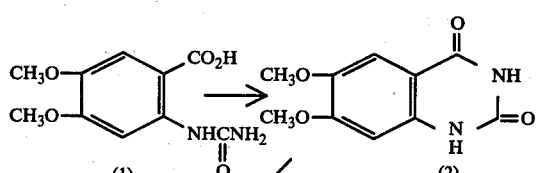

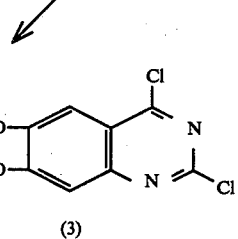

The foregoing procedure of Curd, et al. has been employed in the preparation of various quinazolines disclosed in Hess, U.S. Pat. Nos. 3,511,836 and 3,669,968; Cronin, U.S. Pat. No. 3,517,005; Partyka, et al., U.S. Pat. Nos. 4,001,237 and 4,001,238 and U.S. patent application Ser. No. 659,059 filed Feb. 18, 1976, and now U.S. Pat. No. 4,060,615.

Hess U.S. Pat. No. 3,935,213 describes a process for preparing quinazolines illustrated by formula (6) which involves the use of compounds of formulas (4) and (5) as set forth below.

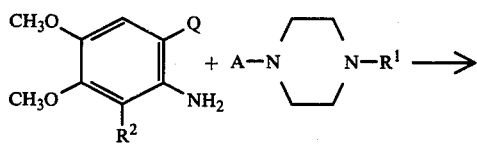

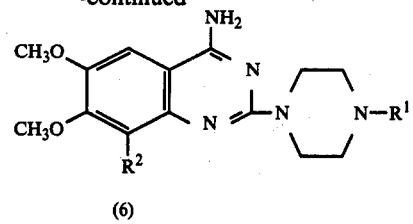

German Pat. No. 2,261,739 (1974)(See Chem. Abs. 81, 84394q (1974) discloses the following synthesis of quinazolin-2,4-diones:

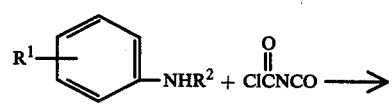

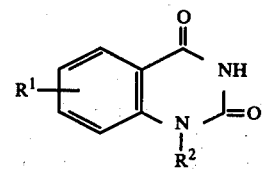

Z. Budesinsky, et al., Coll. Czech. Chem. Commun., 37, 2779 (1972) report that treatment of 1-aryl-3-acylureas (7) with polyphosphoric acid yields 4-aroyl (or alkyl)-2-(1H)-quinazolinones (8).

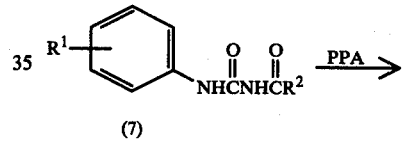

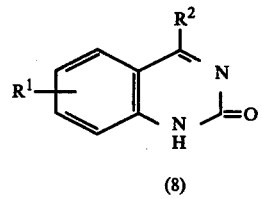

W. Ried,. et al., Chem. Ber., 109, 2706 (1976)(Chem. Abst. 85:191941v (1976) describes the reaction of chloroformamidines of formula (9) with cyanamide derivatives of formula (10) to yield 4-amidinoquinazolines of formula (11).

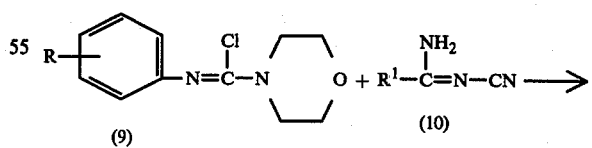

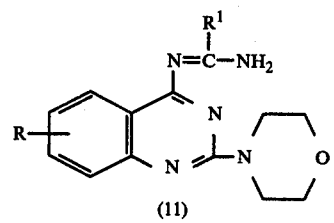

The process of the instant invention for preparing quinazolines characterized by formula (I) below and the Ried, et al. procedure set forth above differ significantly in a number of respects. In the Ried, et al. procedure, the cyano nitrogen in the cyanamide derivative (10) become part of the quinazoline ring (i.e., the number 3 position) whereas in the instant invention, the cyano nitrogen of cyanamide becomes the 4-amino group attached to the quinazoline ring.

SUMMARY OF THE INVENTION

Broadly described, this invention is connected with a new process for the preparation of antihypertensive quinazolines generally typified by formula I

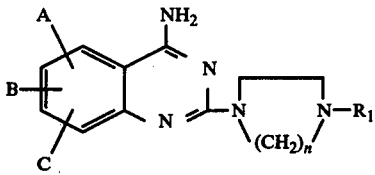

The instant process involves a one-step conversion of novel piperazinyl substituted N-cyano-N'-phenylcarboxamidines to formula I quinazoline products.

DETAILED DESCRIPTION OF THE INVENTION

As indicated hereinabove, one aspect of the instant invention is concerned with a process for preparing quinazoline compounds of formula I

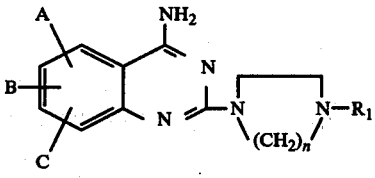

wherein $n$ is equal to 2 or 3;

A is hydrogen or lower alkoxy of 1 to 4 carbon atoms inclusive;

B and C are independently selected from the group consisting of lower alkoxy of 1 to 4 carbon atoms inclusive;

$R_1$ is selected from the group consisting of lower alky; of from 1 to 6 carbon atoms inclusive; $R_2CO$ in which $R_2$ is cycloalkenyl, cycloalkyl, methylcycloalkyl in which cycloalkyl and cycloalkenyl are from 3 to 8 carbon atoms inclusive; hydroalkoxy from 2 to 6 carbon atoms inclusive or phenyl; and $ZC=O$ in which Z is a heterocyclic radical selected from the group consisting of

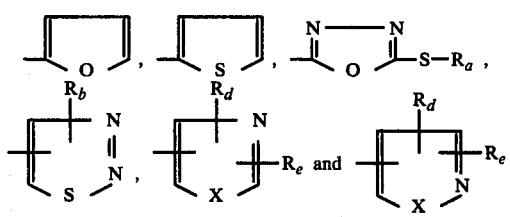

in which X is either oxygen or sulfur, $R_a$ is lower alkyl of 1 to 6 carbon atoms inclusive, $R_b$ is selected from the group consisting of hydrogen, amino, lower alkyl of 1 to 4 carbon atoms inclusive and $NHCO_2R_c$ in which $R_c$ is lower alkyl of 1 to 4 carbon atoms inclusive, $R_d$ and $R_e$ are independently selected from the group consisting of hydrogen, lower alkyl of 1 to 6 carbon atoms inclusive, lower alkoxy of 1 to 6 carbon atoms inclusive, and lower alkylthio of 1 to 6 carbon atoms inclusive which comprises cyclizing a cyanocarboxamidine of formula II

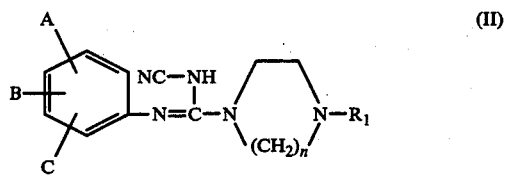

wherein the symbols "A, B, C, and $R_1$" are recited above.

Preferred embodiments of the foregoing process for the preparation of compounds characterized by formula I are those wherein:

(a) The compound of formula II employed is 4-methylpiperazine-1-[N-cyano-N'-(3,4-dimethoxyphenyl)-]carboxamidine;

(b) The compound of formula II employed is 4-(2-furoyl)piperazine-1-[N-cyano-N'-(3,4-dimethoxyphenyl)]carboxamidine;

(c) The compound of formula II employed is 4-(5-methylthio-1,3,4-oxadizaole-2-carbonyl)piperazine-1-[N-cyano-N'-(3,4-dimethoxyphenyl)]carboxamidine;

(d) The cyclization process is carried out by treating the compound of formula II with phosphorus trichloride or phosphorus pentachloride in a solvent amount of phosphorus oxychloride;

(e) The cyclization process is carried out by treating the compound of formula II with phosphorus tribromide or phosphorus pentabromide in a solvent amount of phosphorus oxybromide;

(f) The cyclization process is carried out by treating the compound of formula II with aqueous hydrochloric acid;

(g) The cyclization process is carried out by treating the compound of formula II with hydrogen chloride in phosphorus oxychloride;

(h) The cyclization process is carried out by treating the compound of formula II with a Lewis acid catalyst;

(i) The cyclization process is carried out at a temperature of 25°–125°;

(j) The cyclization process is carried out at a temperature of 70°–100°;

(k) The cyclization process is carried out for a period of 1 to 3 hours at a temperature in the range of 70°–100°.

A preferred embodiment of the present invention is a process for the preparation of a quinazoline of formula Ia

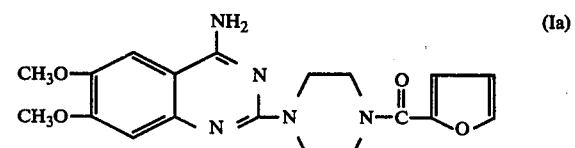

which comprises cyclizing a cyanocarboxamidine having formula IIa

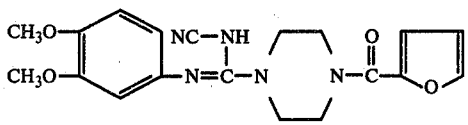
(IIa)

Another preferred embodiment of the present invention is the process for the preparation of a quinazoline of formula Ib

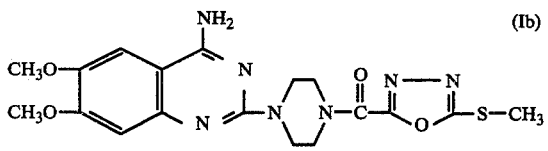
(Ib)

which comprises cyclizing a cyanocarboxamidine having formula IIb

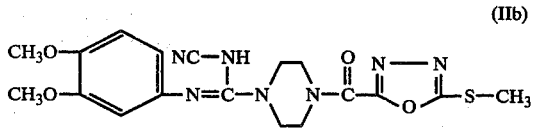
(IIb)

Another preferred embodiment of the present invention is the process for the preparation of a quinazoline of formula Ic

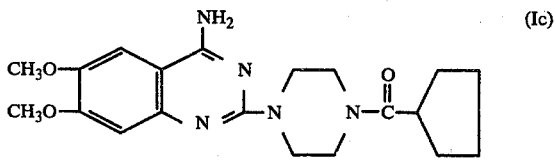
(Ic)

which comprises cyclizing a cyanocarboxamidine having formula IIc

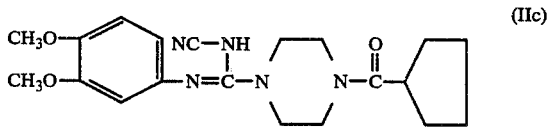
(IIc)

Another preferred embodiment of the present invention is a process for the preparation of a quinazoline of formula Id

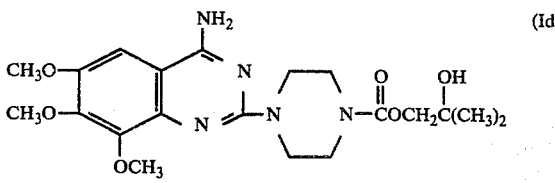
(Id)

which comprises cyclizing a cyanocarboxamidine having formula IId

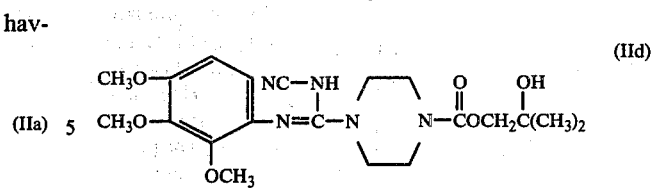
(IId)

Preferred groups of compounds contemplated within the class of cyanocarboxamidines of formula IIa are those wherein:
 (a) the A, B and C substituted phenyl radical is 3,4-dimethoxyphenyl, $n$ is 2, or 3 and $R_1$ is selected from the group consisting of methyl, cyclopentyl, 2-furoyl, 5-methylthio-1,3,4-oxadiazole-2-carbonyl, 2-methyl-2-hydroxypropoxycarbonyl;
 (b) The A, B and C substituted phenyl radical is 2,3,4-trimethoxyphenyl, $n$ is 2 or 3 and $R_1$ is selected from the group consisting of methyl, cyclopentyl, 2-furoyl, 5-methylthio-1,3,4-oxadiazole-2-carbonyl, 2-methyl-2-hydroxypropoxycarbonyl.

Particularly preferred cyanocarboxamidines of formula II are:

4-methylpiperazine-1-[N-cyano-N'-(3,4-dimethoxyphenyl)]-carboxamidine;

4-(2-furoyl)piperazine-1-[N-cyano-N'-(3,4-dimethoxyphenyl)]carboxamidine;

4-(5-methylthio-1,3,4-oxadiazole-2-carbonyl)piperazine-1-[N-cyano-N'-(3,4-dimethoxyphenyl)]-carboxamidine;

4-(2-methyl-2-hydroxypropoxycarbonyl)piperazine-1-[N-cyano-N'-(2,3,4-trimethoxyphenyl)]carboxamidine;

4-(cyclopentylcarbonyl)piperazine-1-[N-cyano-N'-(3,4-dimethoxyphenyl) carboxamidine;

4-(2-furoyl)homopiperazine-1-[N-cyano-N'-(3,4-dimethoxyphenyl]carboxamidine.

It is to be understood that the term "cycloalkyl" as used herein includes cycloalkyl radicals containing 3 to 8 ring carbon atoms inclusive and encompasses such groups as cyclopropyl, cyclobuyl, cyclopentyl, cyclohexyl, cycloheptyl and cycloctyl. The term "methylcycloalkyl" refers to the aforementioned cycloalkyl radicals containing from 3 to 8 ring carbons inclusive having a methyl substituent and encompasses such groups as 1-methylcyclopropyl, 1-methylcyclopentyl, 2-methylcyclopentyl, 3-methylcyclopentyl, 1-methylcyclohexyl, 2-methylcycloheptyl, 4-methylcyclohexyl, and the like. By the term "cycloalkenyl", it is intended to refer to those having from 4 to 8 ring carbon atoms inclusive containing a single ring carbon-carbon double bond encompassing such groups as 1-cyclobutenyl, 1-cyclopentenyl, 2-cyclopentenyl, 3-cyclopentenyl, 1-cyclohexenyl, 2-cyclohexenyl, and the like.

It is also to be understood that by the terms "lower alkyl" and "lower alkoxy", as used herein, it is meant that the carbon chain which comprises these groups include both straight and branched carbon radicals of the designated number of carbon atoms inclusive. Exemplary of carbon chain radicals having 1 to 4 carbon atoms inclusive are methyl, ethyl, propyl, isopropyl, 1-methylpropyl, 2-methylpropyl, and tert.-butyl.

By the term "independently selected", as used herein, it is meant that the recited substituents such as A, B, C, $R_d$, and $R_e$ may or may not be identical.

Conversion of formula II carboxamidines to quinazolines of formula I is carried out by treating the formula II carboxamidines with cyclizing reagents such as phosphorus trichloride or phosphorus pentachloride in a solvent amount of phosphorus oxychloride. Other phosphorus halides and phosphorus oxyhalides such as phosphorus tribromide and phosphorus pentabromide in a solvent amount phosphorus oxybromide may be employed. Ring closure of the carboxamidines of formula II to the quinazoline compounds of formula I is acid catalyzed with reagents such as aqueous hydrochloric acid, hydrogen chloride in phosphorus oxychloride, trichloroacetic acid or Lewis acid catalyst such as $ZnCl_2$, $FeCl_3$, $AlCl_3$, $AlBr_3$, and the like.

With respect to carrying out the reaction with phosphorus halides, approximately equimolar portions of the formula II carboxamidines and phosphorus halides are employed with a convenient solvent amount of phosphorus oxyhalide relative to the amount of carboxamidine starting material. The term "solvent amount" used herein, refers to a quantity of phosphorus oxychloride or phosphorus oxybromide sufficient to provide good mixing and handling characteristics with respect to the reaction mixtures. For this purpose a ratio of from about 2 to 15 ml. of the phosphorus halide for each gram of the carboxamidine reactant of formula II is generally preferred.

Commonly used temperatures for carrying out the cyclization reaction range from about 25°–125° with a particularly preferred temperature range of from about 70°–100°. As will be appreciated by those skilled in the art, reaction time and conditions required for cyclization of the compounds of formula II and formation of the compounds of formula I vary according to several factors such as temperatures and reaction times. For instance, at lower temperatures, long reaction periods are needed, while at higher temperatures, the cyclization reaction is completed in a shorter time. Reaction periods from about 0.5 to 24 hrs. can be used with a period of 1.0 to 3.0 hrs. preferred at a temperature in the range of about 70°–100°.

During the cyclization reaction of the formula II carboxamidines, the cyano carbon acts as a carbonium ion forming a carbon-carbon bond with the benzene nucleus thereby establishing the quinazoline ring while the cyano nitrogen becomes the quinazoline 4-amino group.

The carboxamidines of formula II used as starting materials in the instant process for preparation of quinazoline compounds of formula I are themselves new compounds which are prepared by (a) treating the corresponding urea or thiourea or a salt thereof of formula III

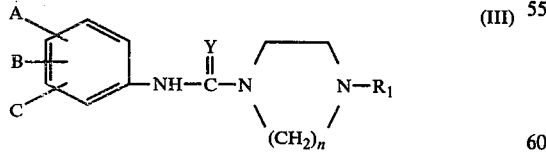

wherein the symbols "A, B, C, n, and $R_1$" are as recited above and Y is sulfur or oxygen with an R—X alkylating reagent in which R is lower alkyl of 1 to 4 carbon atoms inclusive or an aryl derivative containing electron withdrawing groups (e.g., 2,4-dinitrophenyl), X is halogen (e.g., Cl, Br, and I), lower alkyl $SO_4$ of 1 to 4 carbon atoms inclusive, phenyl $SO_3$, $F_3CSO_3$, $FSO_3$, and the like to provide an intermediate of formula IV

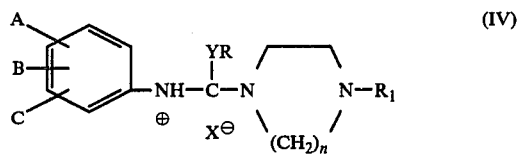

wherein the symbols "A, B, C, n, R, $R_1$, X and Y" are as recited above, and then
(b) reacting the intermediate IV with cyanamide to provide carboxamidines of formula II.

Alkylation of urea and thiourea starting materials of formula III and subsequent reaction with cyanamide is normally carried out in a reaction inert organic solvent. Suitable solvents include dioxane, tetrahydrofuran, dimethyl sulfoxide, diethyl sulfoxide, and alkanol solvents such as methanol, ethanol, or isoamyl alcohol. The reaction can be conducted at temperatures varying within the range of from about 25° to 100° C. for a period of about 0.5 to 24 hrs.

In addition to the above process, alternate methods for preparing carboxamidines of formula II can be employed as depicted in the reaction schemes below.

Method A

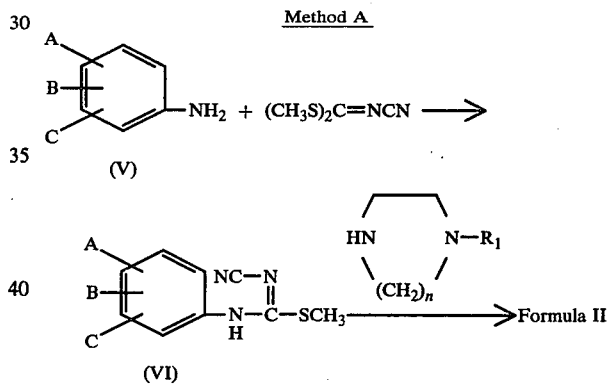

Method B

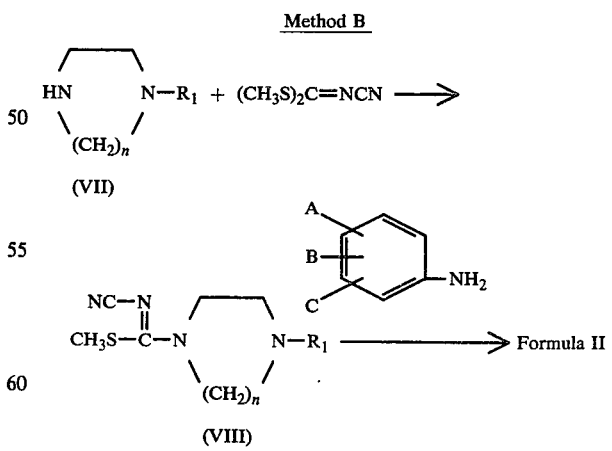

Thus, reaction of $(CH_3S)_2C=NCN$ or chemical equivalents thereof with formula V anilines of formula VII piperazines and homopiperazines wherein the symbols "A, B, C, n and $R_1$" are as previously defined provide cyano intermediates VI and VIII, respectively. Treating the cyano intermediate VI with a compound of Formula VII or the cyano intermediate VIII with an aniline of Formula V affords the formula II carboxamidines.

The formula III urea and thioureas are obtained by reacting appropriately substituted phenylisocyanates and phenylisothiocyanates with N-substituted piperazines and homopiperazines in an inert reaction solvent such as ethanol. Required piperazine and homopiperazine starting material is obtained by conventional procedures; e.g. acylation of piperazine or homopiperazine with

wherein Z is as previously defined.

In addition to being useful intermediates in the preparation of the compounds of formula I, the carboxamidines of formula II are also valuable for their anti-ulcer properties. For instance, 4-(2-furoyl)piperazine-1-[N-cyano-N'-(3,4-dimethoxyphenyl)]carboxamidine and 4-(5-methylthio-1,3,4-oxadiazole-2-carbonyl)piperazine-1-[N-cyano-N'-3,4-dimethoxyphenyl]carboxamidine at a subcutaneous dose of 10 mg/kg and 3 mg/kg body weight, respectively, inhibit acid secretion in the pylorus ligated rat model of Shay, Gastroenterology, 5, 43 (1946).

The following examples further illustrate the present invention and will enable others skilled in the art to understand it more completely. It is to be understood that the invention is not limited solely to the particular examples given below. All temperatures express herein are in degrees centrigrade.

EXAMPLE 1

4-Methylpiperazine-1-[N-cyano-N'-(3,4-dimethoxyphenyl)]carboxamidine

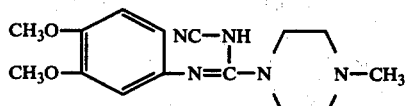

(a) A solution of 3,4-dimethoxyphenyl isothiocyanate (6.8 g., 34.8 mmoles) obtained according to the procedure of G. M. Dyson, et al., J. Chem. Soc., 436 (1927) in 34 ml. of absolute ethanol is added to a stirred solution of N-methylpiperazine (3.49 g., 30.8 mmoles) in 100 ml. of absolute ethanol. After heating the solution to reflux for a 2 hr. period, the solvent is removed under reduced pressure. The semi-solid residue thus obtained is first crystallized from toluene to provide 8.95 g. (87% yield), m.p. 156°-159.5° of the carbothioamide intermediate. Crystallization of this material from nitromethane affords analytically pure 4-methylpiperazine-1-(N-3,4-dimethoxyphenyl)carbothioamide, m.p. 158°-161°.

Anal. Calcd. for $C_{14}H_{21}N_3O_2S$: C, 56.92; H, 7.16; N, 14.23; S, 10.85. Found: C, 56.74; H, 7.38; N, 14.40; S, 10.90.

(b) Methyl iodide (1.2 g., 0.0303 mole) is added to a suspension of 4-methylpiperazine-1-(N-3,4-dimethoxyphenyl)carbothioamide (8.95 g., 0.0303 mole) in 125 ml. of methanol. The reaction mixture is then stirred at reflux temperature for a period of 2 hr. and cooled to 25°. Cyanamide (8.7 g., 0.207 mole) is added to the cooled solution and reflux continued for an additional 16 hr. period. After the solvent is removed under reduced pressure, residual oil is made strongly basic with aqueous 4.0 N sodium hydroxide and then extracted with chloroform. The chloroform extracts are washed with water, saturated brine solution and dried. Concentration of the dried solution affords a residual gum which rubbed under cold toluene provides 4.46 g., (49% yield) of crystalline material, m.p. 155°-158°. Recrystallization from toluene affords analytically pure 4-methylpiperazine-1-[N-cyano-N'-(3,4-dimethoxyphenyl)]carboxamidine, m.p. 160°-163°.

Anal. Calcd. for $C_{15}H_{21}N_5O_2$: C, 59.39; H, 6.98; N, 23.09. Found: C, 58.95; H, 6.83; N, 22.35.

(c) Following the procedure of Example 1(a), but employing an equimolar amount of 3,4-dimethoxyphenylisocyanate in place of 3,4-dimethoxyphenylisothiocyanate, there is produced N-(3,4-dimethoxyphenyl)-4-methyl-1-piperazinecarboxamide. The carboxamide, as its hydrochloride salt, treated with methyl fluorosulfonate and then with cyanamide according to the procedure of Example 1(b) provides 4-methylpiperazine-1-[N-cyano-N'-(3,4-dimethoxyphenyl)]carboxamidine.

EXAMPLE 2

4-(2-Furoyl)piperazine-1-[N-cyano-N'-(3,4-dimethoxyphenyl)]carboxamidine

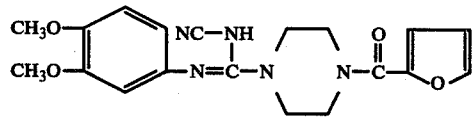

(a) A solution of 3,4-dimethoxyphenyl isothiocyanate (3,21 g., 16.4 mmoles) in 10 ml. of absolute ethanol is added to a stirred solution of 1-(2-furoyl)piperazine (2.96 g., 16.4 mmoles) prepared according to the procedure of M. Desai, et al., Org. Prep. Proced. Int., 8, 85 (1976) in 35 ml. of absolute ethanol and the reaction solution refluxed for a period of 2.5 hr. Concentration of the reaction mixture under reduced pressure provides a dark yellow gum which rubbed under cold ethanol affords 5.39 g., (87% yield) of yellow solid material, m.p. 183°-187°. Crystallization of this material from acetonitrile affords analytically pure 4-(2-furoyl)piperazine-1-(N-3,4-dimethoxyphenylcarbothioamide, m.p. 185°-188°.

Anal. Calcd. for $C_{18}H_{21}N_3O_4S$: C, 57.59; H, 5.64; N, 11.19; S, 8.54. Found: C, 57.23; H, 5.48; N, 11.53; S, 8.54.

(b) To a suspension of 4-(2-furoyl)piperazine-1-(N-3,4-dimethoxyphenyl)carbothioamide (22.0 g., 0.0586 mole) in 400 ml. of methanol is added methyl iodide (8.32 g., 0.0586 mole). The mixture is stirred and refluxed for a period of 2.5 hr. and then cooled to 20°. Cyanamide (18.7 g., 0.445 mole) is added to the cooled solution, and the mixture refluxed for an additional period of 16 hr. and the solvent evaporated under reduced pressure to provide an oily residue which is made strongly basic with aqueous 4.0 N sodium hydroxide. The basic mixture is extracted with chloroform and the chloroform extracts washed first with water and then with saturated brine solution. After drying, the chloroform extract is concentrated under reduced pressure providing a residual gum which is crystallized by rubbing under cold ethanol to afford 11.1 g. (49% yield) of white solid, m.p. 181°–183.5°. Crystallization of this material from ethanol provides analytically pure 4-(2-furoyl)piperazine-1-[N-cyano-N'-(3,4-dimethoxyphenyl)]carboxamidine, m.p. 186.5°–188.5°.

Anal. Calcd. for $C_{19}H_{21}N_5O_4$: C, 59.52; H, 5.52; N, 18.27. Found: C, 59.13; H, 5.40; N, 18.07.

(c) Following the procedure of Example 2(a), but employing equimolar amount of 3,4-dimethoxyphenylisocyanate in place of 3,4-dimethoxyphenylisothiocyanate, there is obtained N-(3,4-dimethoxyphenyl)-4-(2-furoyl)-1-piperazinecarboxamide. Reaction of the carboxamide with methyl fluorosulfonate and then with cyanamide according to the procedure of Example 2(b) provides 4-(2-furoyl)piperazine-1-[N-cyano-N'-(3,4-dimethoxyphenyl)]carboxamidine.

EXAMPLE 3

4-(5-Methylthio-1,3,4-oxadiazole-2-carbonyl)piperazine-1-[N-cyano-N'-(3,4-dimethoxyphenyl)]carboxamidine

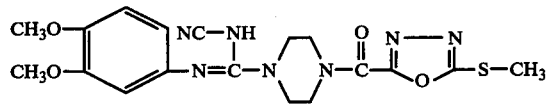

(a) 1-(5-Methylthio-1,3,4-oxadiazole-2-carbonyl)piperazine hydrochloride (5.29 g., 0.02 mole) is first added to a stirred solution of triethylamine (2.02 g., 0.02 mole) in 50 ml. of absolute ethanol followed in 5 min. by a solution of 3,4-dimethoxyphenyl isothiocyanate (3.90 g., 0.02 mole) in 15 ml. of absolute ethanol to provide a pale yellow gummy precipitate. The reaction mixture is heated to reflux (during which time the gum crystallizes), diluted with 28 ml. of absolute ethanol, refluxed for an additional 3 hr. period and filtered. The collected material is washed with absolute ethanol and crystallized from methanol to provide 4.41 g. (52% yield) of 4-methylthio-1,3,4-oxadiazole-2-carbonyl)piperazine-1-(N-3,4-dimethoxyphenyl)carbothioamide, m.p. 143.5°–147°.

Anal. Calcd. for $C_{17}H_{21}N_5O_4S_2$: C, 48.21; H, 5.00, N, 16.54; S, 15.14. Found: C, 48.28; H, 4.90; N, 16.46; S, 15.19.

(b) Methyl iodide (1.06 g., 7.44 mmoles) is added to a suspension of 4-(5-methylthio-1,3,4-oxadiazole-2-carbonyl)piperazine-1-(N-3,4-dimethoxyphenyl)carbothioamide (3.15 g., 7.44 mmoles) in 100 ml. of methanol. The mixture is stirred at reflux temperature for a period of 2.5 hr. and the resulting solution concentrated under reduced pressure to a volume of about 60 ml where a precipitate begins. The mixture is chilled at 0° and filtered to yield 2.93 g. (70% yield) of 1-[methylthio-[N-(3,4-dimethoxyphenyl)]iminocarbonyl]-4-(5-methylthio-1,3,4-oxadiazole-2-carbonyl)piperazine hydroiodide, m.p. 180.5°–185° (dec.). Crystallization from ethanol provided analytically pure hydroiodide intermediate, m.p. 184°–187° (dec).

Anal. Calcd. for $C_{18}H_{23}N_5O_4S_2$·HI: C, 38.24; H, 4.28; N, 12.39. Found 38.49; H, 4.44; N, 12.01.

(c) Cyanamide (0.66 g., 15.7 mmoles) is added to 1-[methylthio-[N-(3,4-dimethoxyphenyl)]iminocarbonyl]-4-(5-methylthio-1,3,4-oxadiazole-2-carbonyl)-piperazine (2.44 g., 5.58 mmoles) free base in 35 ml. of absolute ethanol. The mixture is stirred at reflux temperature for a period of 20 hr., cooled in an ice bath and filtered to provide 1.12 g. (49% yield) of off-white solid, m.p. 175°–181°. Crystallization of this material from methanol affords analytically pure 4-(5-methylthio-1,3,4-oxadiazole-2-carbonyl)piperazine-1-[N-cyano-N'-(3,4-dimethoxyphenyl)]carboxamidine, m.p. 174-178°.

Anal. Calcd. for $C_{18}H_{21}N_7O_4S$: C, 50.12; H, 4.90; N, 22.73. Found: C, 50.08; H, 4.73; N, 22.57.

(d) Following the procedure of Example 3(a), but employing an equimolar amount of 3,4-dimethoxyphenylisocyanate in place of 3,4-dimethoxyphenylisothiocyanate, there is obtained N-(3,4-dimethoxyphenyl)-4-(5-methylthio-1,3,4-oxadiazole-2-carbonyl)-1-piperazine carboxamide. Reaction of the carboxamide with methyl fluorosulfonate and then with cyanamide according to the procedures of Examples 3(b) and 3(c), respectively, provides 4-(5-methylthio-1,3,4-oxadiazole-2-carbonyl)piperazine-1-[N-cyano-N'-(3,4-dimethoxyphenyl)]carboxamidine.

EXAMPLE 4

4-(2-Methyl-2-hydroxypropoxycarbonyl)piperazine-1-[N-cyano-N'-2,3,4-trimethoxyphenyl]carboxamidine

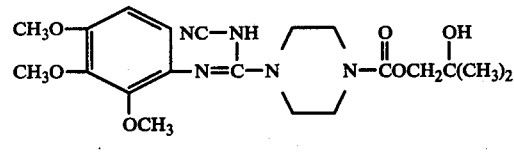

Reaction of 2,3,4-trimethoxyphenylisothiocyanate with 1-(2-methyl-2-hydroxypropoxycarbonyl)piperazine according to the procedure of Example 1(b) provides 4-(2-methyl-2-hydroxypropoxycarbonyl)piperazine-1-(N-2,3,4-trimethoxyphenyl)carbothioamide. Subsequent reaction of the carbothioamide with methyl iodide and then with cyanamide according to the procedure of Example 1(b) accords 4-(2-methyl-2-hydroxypropoxycarbonyl)piperazine-1-[N-cyano-N'-2,3,4-trimethoxyphenyl]carboxamidine.

EXAMPLE 5

4-(Cyclopentylcarbonyl)piperazine-1-[N-cyano-N'-(3,4-dimethoxyphenyl)]carboxamidine

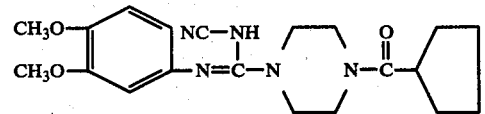

Following the procedure of Example 1(a) but employing an equimolar amount of N-(cyclopentylcarbonyl)piperazine in place of N-methylpiperazine, there is produced 4-(cyclopentylcarbonyl)piperazine-1-(N-3,4-dimethoxyphenyl)carbothioamide. Reaction of the carbothioamide with methyl iodide and then with cyanamide according to the procedure of Example 1(b) affords 4-(cyclopentylcarbonyl)piperazine-1-[N-cyano-N'-(3,4-dimethoxyphenyl)]carboxamidine.

EXAMPLE 6

4-(2-Furoyl)homopiperazine-1-[N-cyano-N'-(3,4-dimethoxyphenyl)]carboxamidine

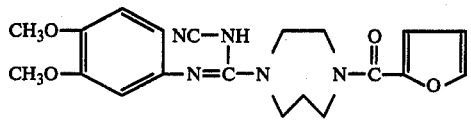

Following the procedure of Example 1(a-b) but substituting 1-(2-furoyl)homopiperazine for 1-(2-furoyl)piperazine, the title compound is obtained.

EXAMPLE 7

4-Amino-6,7-dimethoxy-2-(4-methylpiperazin-1-yl)quinazoline dihydrochloride

Phosphorus pentachloride (0.31 g., 1.48 mmoles) is added with stirring to 10 ml. of phosphorous oxychloride followed in 5 min. by 4-methylpiperazine-1-[N-cyano-N'-(3,4-dimethoxyphenyl)]carboxamidine of Example 1 (0.45 g., 1.48 mmoles). The reaction mixture is heated at 95°–98° for a period of 2.5 hr. during which time a yellow gum forms and changes to a suspended solid by the end of the heating period. The reaction mixture is then cooled to 30° and excess phosphorus oxychloride removed under reduced pressure to provide a residual material which is treated cautiously with ice/water. The aqueous phase is filtered and the filtrate concentrated under reduced pressure to provide a brown oil which is crystallized by rubbing under cold acetone. Insoluble material is collected and crystallized from methanol to afford 0.175 g., 31% yield of 4-amino-6,7-dimethoxy-2-(4-methylpiperazin-1-yl)quinazoline dihydrochloride, m.p. 280°–282° (dec) identical with the sample prepared according to the procedure described in U.S. Pat. No. 3,511,836.

EXAMPLE 8

4-Amino-6,7-dimethoxy-2-[4-(2-furoyl)piperazine-1-yl]quinazoline hydrochloride

Hydrogen chloride gas is bubbled for a period of 8 min. into a cold, stirred mixture of 4-(2-furoyl)piperazine-1-[N-cyano-N'-(3,4-dimethoxyphenyl)]carboxamidine of Example 2 (3.0 g., 7.82 mmoles) in 45 ml. of phosphorus oxychloride. After addition of the hydrogen chloride gas, the reaction mixture is stirred at 25°–30° for 10 min. and then heated at 70°–75° for a period of 75 min. during which time a gummy solid separates. The reaction mixture is cooled to 30°, the excess phosphorus oxychloride removed under reduced pressure and residual material rubbed under ice/water to provide a solid. The solid is collected to afford 2.76 g. (84% yield) of 4-amino-6,7-dimethoxy-2-[4-(2-furoyl)piperazin-1-yl]quinazoline hydrochloride identical with a sample prepared according to the procedure of U.S. Pat. No. 3,511,836.

EXAMPLE 9

4-Amino-6,7-dimethoxy-2-[4-(5-methylthio-1,3,4-oxadiazolecarbonyl)piperazin-1-yl]quinazoline hydrochloride Hydrogen chloride gas is bubbled for a period of 4 min. into a cold, stirred mixture of 4-(5-methylthio-1,3,4-oxadiazole-2-carbonyl)piperazin-1-[N-cyano-N'-(3,4-dimethoxyphenyl)]carboxamidine of Example 3 (0.16 g., 0.37 mmoles) in 6 ml. of phosphorus oxychloride and the mixture then stirred at 25°–30° for an additional 8 min. period and finally heated to 72°–75° for a period of 75 min. during which time a pale yellow solid precipitates. After the heating period, the mixture is cooled to 30°, excess phosphorus oxychloride removed under reduced pressure and residual solid rubbed under ice/water and collected to provide 4-amino-6,7-dimethoxy-2-[4-(5-methylthio-1,3,4-oxadiazole-2-carbonyl)-piperazin-1-yl]quinazoline hydrochloride in 95% yield identical to a sample prepared according to the procedure of U.S. Pat. No. 4,001,238.

EXAMPLE 10

The cyclization procedure illustrated in Examples 1–3 is repeated with the following cyanocarboxamides:

4-(2-methyl-2-hydroxypropoxycarbonyl)piperazine-1-[N-cyano-N'-(2,3,4-trimethoxyphenyl)]carboxamidine, 4-(cyclopentylcarbonyl)piperazine-1-[N-cyano-N'-(3,4-dimethoxyphenyl)]carboxamidine, 4-(2-furoyl)homopiperazine-1-[N-cyano-N'-(3,4-dimethoxyphenyl)]carboxamidine, to produce respectively, (a) 4-amino-6,7,8-trimethoxy-2-[4-(2-methyl-2hydroxypropoxycarbonyl)piperazin-1-yl]quinazoline,
(b) 4-amino-6,7-dimethoxy-2-[4-(cyclopentylcarbonyl)piperazin-1-yl]quinazoline,
(c) 4-amino-6,7-dimethoxy-2-[4-(2-furoylhomopiperazin-1-yl)]quinazoline.

What is claimed is:

1. A compound selected from the group consisting of cyanocarboxamidines having formula II

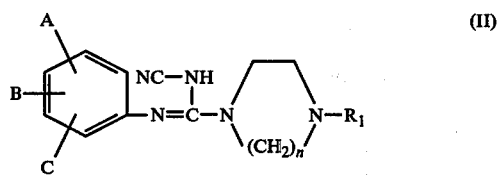

wherein $n$ is equal to 2 to 3,

A is hydrogen or lower alkyl of 1 to 4 carbon atoms inclusive;

B and C are independently selected from the group consisting of lower alkoxy of 1 to 4 carbon atoms inclusive, $R_1$ is selected from the group consisting of lower alkyl of from 1 to 6 carbon atoms inclusive, $R_2C=O$ in which $R_2$ is cycloalkenyl, cycloalkyl, methylcycloalkyl in which cycloalkyl and cycloalkenyl are from 3 to 8 carbon atoms inclusive, hydroxyalkoxy of from 2 to 6 carbon atoms inclusive or phenyl, and $ZC=O$ in which Z is a heterocyclic radical selected from the group consisting of

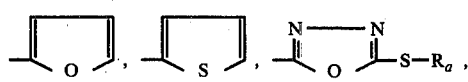

-continued

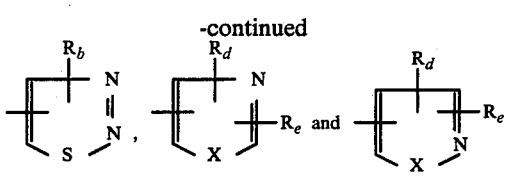

in which X is either oxygen or sulfur, $R_a$ is lower alkyl of 1 to 6 carbon atoms inclusive, $R_b$ is selected from the group consisting of hydrogen, amino, lower alkyl of 1 to 4 carbon atoms inclusive and $NHCO_2R_c$ in which $R_c$ is lower alkyl of 1 to 4 carbon atoms inclusive, $R_d$ and $R_e$ are independently selected from the group consisting of hydrogen, lower alkyl of 1 to 6 carbon atoms inclusive, lower alkoxy of 1 to 6 carbon atoms inclusive, and lower alkylthio of 1 to 6 carbon atoms inclusive.

2. The compound of formula II which is 4-methyl-piperazine-1-[N-cyano-N'-(3,4-dimethoxyphenyl)]carboxamidine.

3. The compound of formula II which is 4-(2-furoyl)-piperazine-1-[N-cyano-N'-(3,4-dimethoxyphenyl)]carboxamidine.

4. The compound of formula II which is 4-(5-methylthio-1,3,4-oxadiazole-2-carbonyl)piperazine-1-[N-cyano-N'-(3,4-dimethoxyphenyl)]carboxamidine.

5. A process for preparing a quinazoline compound of formula I

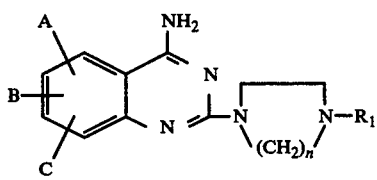

wherein
n is equal to 2 or 3;
A is hydrogen or lower alkoxy of 1 to 4 carbon atoms inclusive;
B and C are independently selected from the group consisting of lower alkoxy of 1 to 4 carbon atoms inclusive;
$R_1$ is selected from the group consisting of lower alkyl of from 1 to 6 carbon atoms inclusive; $R_2CO$ in which $R_2$ is cycloalkenyl, cycloalkyl, methylcycloalkyl in which cycloalkyl and cycloalkenyl are from 3 to 8 carbon atoms inclusive; hydroxyalkoxy from 2 to 6 carbon atoms inclusive or phenyl; and ZC=O in which Z is a heterocyclic radical selected from the group consisting of

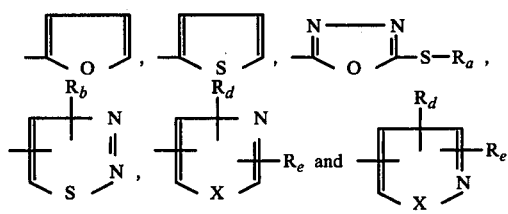

in which X is either oxygen or sulfur, $R_a$ is lower alkyl of 1 to 6 carbon atoms inclusive, $R_b$ is selected from the group consisting of hydrogen, amino, lower alkyl of 1 to 4 carbon atoms inclusive and $NHCO_2R_c$ in which $R_c$ is lower alkyl of 1 to 4 carbon atoms inclusive, $R_d$ and $R_e$ are independently selected from the group consisting of hydrogen, lower alkyl of 1 to 6 carbon atoms inclusive, lower alkoxy of 1 to 6 carbon atoms inclusive, and lower alkylthio of 1 to 6 carbon atoms inclusive which comprises cyclizing a cyanocarboxamidine of formula II

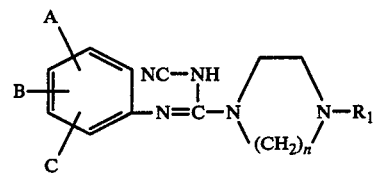

wherein the symbols "A, B, C, n and $R_1$" are as recited above.

6. The process of claim 5 wherein the compound of formula II employed is 4-methylpiperazine-1-[N-cyano-N'-(3,4-dimethoxyphenyl)]carboxamidine.

7. The process of claim 5 wherein the compound of formula II employed is 4-(2-furoyl)piperazine-1-[N-cyano-N'-(3,4-dimethoxyphenyl)]carboxamidine.

8. The process of claim 5 wherein the compound of formula II employed is 4-(5-methylthio-1,3,4-oxadiazole-2-carbonyl)piperazine-1-[N-cyano-N'-(3,4-dimethoxyphenyl)]carboxamidine.

9. The process of claim 5 wherein the cyclization process is carried out by treating the compound of formula II with phosphorus trichloride or phosphorus pentachloride in a solvent amount of phosphorus oxychloride.

10. The process of claim 5 wherein the cyclization process is carried out by treating the compound of formula II with phosphorus tribromide or phosphorus pentabromide in a solvent amount of phosphorus oxybromide.

11. The process of claim 5 wherein the cyclization process is carried out by treating the compound of formula II with aqueous hydrochloric acid.

12. The process of claim 5 wherein the cyclization process is carried out by treating the compound of formula II with hydrogen chloride in phosphorus oxychloride.

13. The process of claim 5 wherein the cyclization process is carried out by treating the compound of formula II with a Lewis acid catalyst.

14. The process of claim 5 wherein the cyclization process is carried out at a temperature of 25°–125°.

15. The process of claim 5 wherein the cyclization process is carried out at a temperature of 70°–100°.

16. The process of claim 5 wherein the cyclization process is carried out for a period at 1 to 3 hours at a temperature in the range of 70°–100°.

17. A process for the preparation of a quinazoline of formula Ia

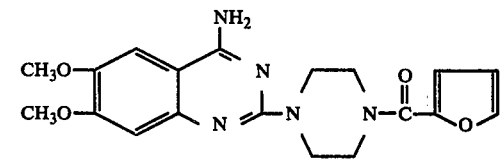

which comprises cyclizing a cyanocarboxamidine having formula IIa

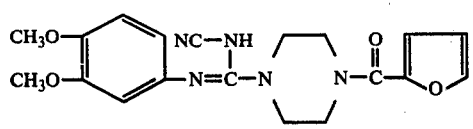

18. A process for the preparation of a quinazoline of formula Ib

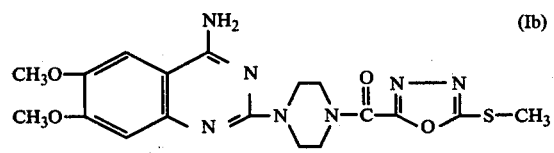

which comprises cyclizing a cyanocarboxamidine having formula IIb

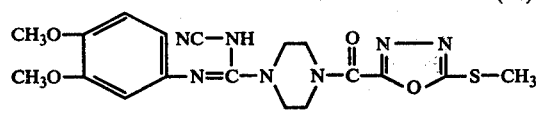

19. A process for the preparation of a quinazoline of formula Ic

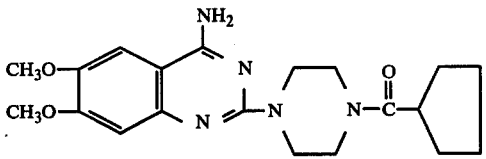

which comprises cyclizing a cyanocarboxamidine having formula IIc

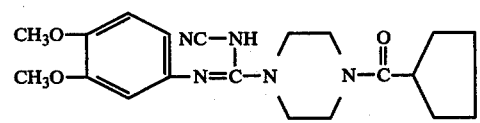

20. A process for the preparation of a quinazoline of formula Id

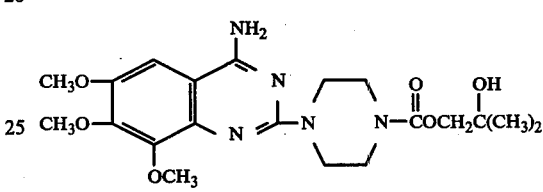

which comprises cyclizing a cyanocarboxamidine having formula IId

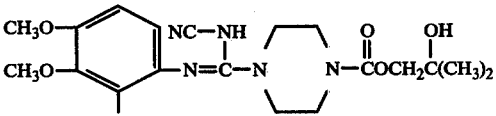

* * * * *